United States Patent
Okamoto et al.

(10) Patent No.: US 6,992,229 B2
(45) Date of Patent: Jan. 31, 2006

(54) METHOD FOR PURIFYING A FLUORINATED HYDROXYL COMPOUND

(75) Inventors: Hidekazu Okamoto, Yokohama (JP); Akihiro Wada, Ichihara (JP); Toshihiko Toma, Ichihara (JP); Nobuyuki Yamagishi, Ichihara (JP)

(73) Assignee: Asahi Glass Company, Limited, Tokyo (JP)

( * ) Notice: Subject to any disclaimer, the term of this patent is extended or adjusted under 35 U.S.C. 154(b) by 300 days.

(21) Appl. No.: 10/298,652

(22) Filed: Nov. 19, 2002

(65) Prior Publication Data

US 2003/0069454 A1   Apr. 10, 2003

Related U.S. Application Data

(63) Continuation of application No. 10/077,794, filed on Feb. 20, 2002, which is a continuation of application No. PCT/JP00/05569, filed on Aug. 18, 2000.

(30) Foreign Application Priority Data

Aug. 20, 1999  (JP)  ................................. 11-233608

(51) Int. Cl.
*C07C 31/34* (2006.01)
*C07C 31/38* (2006.01)
*C07C 31/42* (2006.01)

(52) U.S. Cl. .................. 568/842; 568/841; 570/123; 570/124; 570/134; 570/136; 570/140; 570/142; 570/171; 570/175; 570/177; 570/178

(58) Field of Classification Search ................ 568/842, 568/841; 570/123, 124, 134, 136, 140, 142, 570/171, 175, 177, 178; 210/767
See application file for complete search history.

(56) References Cited

U.S. PATENT DOCUMENTS

| | | | |
|---|---|---|---|
| 4,156,791 | A | 5/1979 | Childs |
| 4,219,680 | A | 8/1980 | Koenig et al. |
| 4,224,112 | A | 9/1980 | Childs |
| 4,236,975 | A | 12/1980 | Childs |
| 4,346,250 | A | 8/1982 | Satokawa et al. |
| 5,227,540 | A | 7/1993 | Knaup |
| 5,233,098 | A | 8/1993 | Nakazora et al. |

FOREIGN PATENT DOCUMENTS

| | | |
|---|---|---|
| EP | 0 992 476 A2 | 12/1999 |
| EP | 0 968 989 A2 | 1/2000 |
| JP | 6-271495 | 9/1994 |
| JP | 2000-247919 | 9/2000 |

OTHER PUBLICATIONS

Derwent Publications, AN 1994-347078 [43], XP-002220481, JP 06-271495, Sep. 27, 1994.
U.S. Appl. No. 10/077,794, filed Feb. 20, 2002, Wada et al.
U.S. Appl. No. 10/131,187, filed Apr. 25, 2002, Okamoto.
U.S. Appl. No. 10/298,652, filed Nov. 19, 2002, Okamoto et al.
U.S. Appl. No. 10/028,827, filed Dec. 28, 2001, Wada et al.
U.S. Appl. No. 10/370,507, filed Feb. 24, 2003, Okamoto.

*Primary Examiner*—Elvis O. Price
(74) *Attorney, Agent, or Firm*—Oblon, Spivak, McClelland, Maier & Neustadt, P.C.

(57) ABSTRACT

The present invention has an object to provide a method for purifying a fluorinated hydroxyl compound of the formula 1 safely in a high yield under industrially practical conditions. Namely, a mixture containing a fluorinated hydroxyl compound of $R^f$—$CR^1R^2$—OH (Formula 1, wherein $R^f$ is a $C_{1-20}$ polyfluoroalkyl group, and each of $R^1$ and $R^2$ is a hydrogen atom or a $C_{1-3}$ alkyl group) such as 2,2,3,3-tetrafluoropropanol, and a compound having an unshared electron pair, is distilled by heating in the presence of a solid acid catalyst such as a cation exchange resin catalyst, or by adding a proton source such as water.

17 Claims, No Drawings

METHOD FOR PURIFYING A FLUORINATED HYDROXYL COMPOUND

This application is a Continuation Application of U.S. application Ser. No. 10/077,794, filed Feb. 20, 2002, pending, which is a continuation application of PCT application PCT/JP00/05569, filed Aug. 18, 2000, pending, which was not published under Article 21(2) in English.

TECHNICAL FIELD

The present invention relates to a method for purifying a fluorinated hydroxyl compound.

BACKGROUND ART

A fluorinated hydroxyl compound is useful as a water and oil repellent, a surfactant or an intermediate for a color developing material for photograph (JP-A-54-154707). Further, a fluorinated hydroxyl compound does not dissolve a plastic substrate and thus is useful as a solvent for e.g. a dye for an optical recording material (JP-A-4-8585, JP-A-5-258346).

Heretofore, purification of a fluorinated hydroxyl compound has been carried out by distillation. However, when a compound having an unshared electron pair (hereinafter referred to also as an unshared electron pair compound) is included in the process for producing a fluorinated hydroxyl compound, such an unshared electron pair compound interacts with the fluorinated hydroxyl compound, whereby there has been a problem that it can not be separated by usual distillation separation. For example, when the unshared electron pair compound is an aliphatic alcohol such as t-butanol, there has been a problem that it can not be separated by usual distillation, even if there is a difference in boiling point between the fluorinated hydroxyl compound and the aliphatic alcohol.

Further, a method has been proposed wherein methanol is reacted with tetrafluoroethylene or hexafluoropropylene in the presence of a polymerization initiator to obtain a reaction product containing a fluorinated alcohol, which is then heated to decompose an unreacted polymerization initiator, followed by distillation (EP968989A). However, this method requires heating of the reaction product, and there has been a problem such that the unreacted polymerization initiator can not be recovered.

Further, a purification method is also proposed wherein a fluorinated alcohol containing water in an amount of not more than 2000 ppm, is distilled to remove water azeotropically or pseudoazeotropically to obtain a fluorinated alcohol as the residue (EP992476A). However, the fluorinated alcohol in such a method contains no unshared electron pair compound, and in such a method, the fluorinated alcohol is obtained as a residue, whereby there has been a problem that impurities which are likely to remain as evaporation residues, will remain in the fluorinated alcohol.

DISCLOSURE OF THE INVENTION

The present invention has been made to solve the above problems and is the following invention which provides a method for purifying a fluorinated hydroxyl compound, which is industrially practical and can be carried out by a simple operation in good yield.

Namely, the present invention provides a method for purifying a fluorinated hydroxyl compound, which comprises distilling a mixture containing a fluorinated hydroxyl compound of the following formula 1 and a compound having an unshared electron pair, by heating in the presence of a solid acid catalyst or by adding a proton source, to separate the compound having an unshared electron pair from the mixture:

$$R^f\text{—}CR^1R^2\text{—}OH \qquad \text{Formula 1}$$

provided that the symbols in the formula have the following meanings:
$R^f$: a $C_{1\text{-}20}$ polyfluoroalkyl group; and
$R^1$ and $R^2$: each independently, a hydrogen atom or a $C_{1\text{-}3}$ alkyl group.

BEST MODE FOR CARRYING OUT THE INVENTION $R^f$ in the fluorinated hydroxyl compound (formula 1) is a $C_{1\text{-}20}$ polyfluoroalkyl group. The polyfluoroalkyl group is meant for a group having at least two hydrogen atoms of an alkyl group substituted by fluorine atoms. The polyfluoroalkyl group may be of a straight chain structure or a branched structure. The number of carbon atoms of the polyfluoroalkyl group is preferably from 1 to 4. Further, it is preferred that from 1 to 3, particularly preferably from 1 to 2, fluorine atoms are bonded to the carbon atom which is directly bonded to —$CR^1R^2$—OH of the polyfluoroalkyl group. Examples of the polyfluoroalkyl group may be the groups disclosed in the examples of the fluorinated hydroxyl compound (Formula 1).

Each of $R^1$ and $R^2$ which are independent of each other, is a hydrogen atom or a $C_{1\text{-}3}$ alkyl group. The $C_{1\text{-}3}$ alkyl group may be a methyl group, an ethyl group, a n-propyl group or an isopropyl group.

The following compounds may be mentioned as specific examples of the fluorinated hydroxyl compound (Formula 1):

$CF_3CH_2OH$,
$CF_3CF_2CH_2OH$,
$CF_3(CF_2)_2CH_2OH$,
$CF_3(CF_2)_3CH_2OH$,
$HCF_2CH_2OH$,
$H(CF_2)_2CH_2OH$,
$H(CF_2)_3CH_2OH$,
$H(CF_2)_4CH_2OH$,
$CHF_2CF_2CH(CH_3)OH$,
$CHF_2CF_2C(CH_3)_2OH$,
$CF_3CHFCF_2CH_2OH$,
$CF_3CHFCF_2CH(CH_3)OH$,
$CF_3CHFCF_2C(CH_3)_2OH$.

The unshared electron pair compound may, for example, be an alcohol compound other than the fluorinated hydroxyl compound (Formula 1), an amine compound or a thiol compound, and an alcohol compound other than the fluorinated hydroxyl compound (Formula 1) is preferred. The alcohol compound (Formula 1) is preferably an aliphatic alcohol compound, particularly preferably an alcohol compound having a saturated hydrocarbon group, especially preferred is an aliphatic tertiary alcohol compound having a saturated hydrocarbon group. Specific examples of the alcohol compound include methanol, ethanol, isopropyl alcohol, propanol, tert-butanol, sec-butanol and n-butanol. Methanol and tert-butanol are particularly preferred, and especially preferred is tert-butanol.

In the fluorinated hydroxyl compound (Formula 1), the polyfluoroalkyl group and the hydroxyl group are close to each other, and accordingly, there is a nature that the acidity of the compound is strong. Accordingly, it is considered that if an unshared electron pair compound is co-present, such an unshared electron pair and the fluorinated hydroxyl compound (Formula 1) will form a hydrogen bond to form a high boiling composite, and this composite will remain in the still pot until the later stage of distillation in an equilibrium state with the unshared electron pair compound, whereby separation by distillation can not satisfactorily be carried out. And, there has been a problem that such a composite may cause an adverse effect, when the fluorinated hydroxyl compound is used for other applications. According to the present invention, this unshared electron pair compound can effectively be removed.

In the present specification, the mixture is a mixture containing the fluorinated hydroxyl compound (Formula 1) and the unshared electron pair compound. The amount of the unshared electron pair compound is preferably from 0.01 wt % (mass %) to 25 wt % (mass %), particularly preferably from 0.05 wt % (mass %) to 3 wt % (mass %), based on the fluorinated hydroxyl compound (Formula 1).

The mixture is preferably a reaction crude product containing an alcohol compound (Formula 3) and a compound (Formula 1a) formed by heating a perfluoroolefin compound (Formula 2) and an alcohol compound (Formula 3) in the presence of a radical initiator:

$R^{f1}CF=CF_2$ <span>Formula 2</span>

$CHR^1R^2OH$ <span>Formula 3</span>

$R^{f1}CHFCF_2R^1R^2OH$ <span>Formula 1a</span> provided that the symbols in the formulae have the following meanings:
$R^{f1}$: a fluorine atom or a $C_{1-8}$ polyfluoroalkyl group; and
$R^1$ and $R^2$: the same meaning as above.

Here, the compound (Formula 1a) is preferably at least one member selected from the 2,2,3,3-tetrafluoropropanol, 2,2,3,3-tetrafluoro-1-methylpropanol, 2,2,3,3-tetrafluoro-1,1-dimethylpropanol, 2,2,3,4,4,4-hexafluorobutanol, 2,2,3,4,4,4-hexafluoro-1-methylbutanol and 2,2,3,4,4,4-hexafluoro-1,1-dimethylbutanol.

The radical initiator may, for example, be an azo compound or a peroxyether compound. From the viewpoint of the half-value period and the reaction temperature, a peroxyether compound is preferred, and a commonly employed dialkyl peroxyether compound is particularly preferred.

The reaction crude product is meant for a reaction product not subjected to e.g. chromatography or distillation. In a case where a solid content is included in the reaction crude product, the solid content may be removed by an operation such as filtration. The purification method of the present invention is an excellent method whereby the reaction crude product is not required to be heated or the like prior to the distillation and may be distilled substantially as it is (namely, as it contains an unreacted radical initiator) whereby a fluorinated hydroxyl compound having a high purity can be obtained.

In the present invention, purification is carried out by distilling the mixture by heating it in the presence of a solid acid catalyst (Method 1) or by distilling the mixture by adding a proton source thereto (Method 2).

The solid acid catalyst in Method 1 may, for example, be $SiO_2 \cdot Al_2O_3$, $SiO_2 \cdot MgO_2$, $SiO_2 \cdot ZrO_2$, $Al_2O_3 \cdot B_2O_3$, $Al_2O_3$, zeolite, heteropoly acid, a metal phosphate, a metal sulfate, a solid phosphoric acid catalyst ($H_3PO_4$/diatomaceous earth), a cation exchange resin catalyst, $SbF_5$ supported on an oxide, a sulfate supported on zirconium or a layered silicate.

Zeolite is preferably of a proton type. Specifically, A-type zeolite, ZSM-5 type zeolite, mordenite, X-type zeolite or Y-type zeolite may, for example, be mentioned.

Specific examples of the heteropoly acid include $H_3PW_{12}O_{40}$, $H_3PMo_{12}O_{40}$ and $Cs_{2.5}H_{0.5}PW_{12}O_{40}$.

The metal phosphate may, for example, be $BPO_4$, $Ca_3(PO_4)_2$, $Zr(HPO_4)_2$, $AlPO_4$, $Cd_3(PO_4)_2$, $CePO_4$, $Zn_3(PO_4)_2$ or $Ca_{10}(PO_4)_6(OH)_2$. Further, the metal phosphate may be supported on e.g. $SiO_2$.

The metal sulfate may, for example, be $MgSO_4$, $CaSO_4$, $ZnSO_4$, $Al_2(SO_4)_3$, $CuSO_4$ or $FeSO_4$. Further, such a metal sulfate may be supported on e.g. $SiO_2$ or $ZrO_2$.

From the viewpoint of the reactivity, the cation exchange resin catalyst is preferably a cation exchange resin catalyst having super strong acid points, such as a fluorine resin catalyst having sulfonic groups or a fluorine resin catalyst having carboxyl groups. The cation exchange resin catalyst is commercially available, and for example, Nafion (tradename, manufactured by E.I. DuPont), SAC-13 (tradename, manufactured by E.I. DuPont) or NR-40 (tradename, manufactured by E.I. DuPont) may, for example, be mentioned.

The layer silicate may, for example, be bentonite, montmorillonite, andalusite or kaolin.

The shape of such a solid acid catalyst is preferably powdery, particulate or honeycomb, particularly preferably particulate from the viewpoint of efficiency in separation. Further, as the solid acid catalyst, a cation exchange resin catalyst or zeolite is preferred, which has high activity and can easily be regenerated. Zeolite is particularly preferred.

In Method 1, the mixture is heated in the presence of the solid acid catalyst. The solid acid catalyst is capable of chemically changing the unshared electron pair compound. In a case where the unshared electron pair compound is an aliphatic alcohol compound, it may be decomposed and changed into an olefin, or it undergoes dehydration condensation with the fluorinated hydroxyl compound (Formula 1) to form an ether compound. An olefin or an ether compound is usually a compound which can readily be separated by distillation from the fluorinated hydroxyl compound (Formula 1).

In Method 1, the solid acid catalyst is added to the mixture preferably all at once or successively, and from the viewpoint of the operation, it is added more preferably all at once. Further, the distillation may be carried out after the addition of the solid acid catalyst, or the distillation may be carried out while adding the solid acid catalyst.

The amount of the solid acid catalyst is preferably from 0.5 to 100 wt % (mass %), particularly preferably from 1.0 to 50 wt % (mass %), based on the fluorinated hydroxyl compound (Formula 1). Further, the heating temperature is preferably from 60 to 150° C., and the heating time is preferably from 0.5 to 10 hours. The pressure during the heating is preferably from 0.01 to 0.5 MPa.

As the distillation conditions in Method 1, conditions for usual distillation for purification of such a fluorinated hydroxyl compound may be employed. Usually, the tower top temperature is preferably from 40 to 200° C., and the pressure is preferably from 0.01 to 0.5 MPa (gauge pressure).

In Method 2, a proton source is added to the mixture, followed by distillation. Such a proton source is considered to facilitate separation by distillation by hindering formation of a hydrogen bond between the fluorinated hydroxyl compound and the unshared electron pair compound.

The proton source may, for example, be water, hydrogen fluoride, hydrogen chloride or hydrogen bromide, and water is preferred. Water has a large ability to hinder formation of a complex and can easily be separated from other compounds, and it has a merit of preventing corrosion of the reactor. The amount of the proton source is preferably from 0.01 to 30 wt % (mass %), more preferably from 0.1 to 10 wt % (mass %), most preferably from 1 to 10 wt % (mass %), based on the fluorinated hydroxyl compound (Formula 1). If the amount of water is too small, the effect to hinder formation of a complex is small, whereby purification by separation of the fluorinated hydroxyl compound may not proceed satisfactorily.

The proton source may be added to the mixture all at once or successively. Successive addition is preferred from such a viewpoint that the amount of addition can be reduced.

Further, in Method 2, when water is used as the proton source, it is preferred that the nature of the mixture is adjusted towards the acidic side, whereby separation by distillation will be facilitated.

The distillation temperature in Method 2 is preferably from 50 to 250° C., more preferably from 50 to 200° C. for an industrial operation. Further, when water is used as the proton source, the distillation temperature is preferably from 50 to 250° C., particularly preferably from 50 to 130° C. from the viewpoint of industrial operation. In the distillation, it is preferred to isolate the fluorinated hydroxyl compound (Formula 1) as the main fraction, after distilling off a low boiling fraction. The addition of a proton source hinders formation of a complex, whereby separation is facilitated between fractions of the fluorinated hydroxyl compound (Formula 1) and the unshared electron pair compound, and the fluorinated hydroxyl compound (Formula 1) having a high purity can be obtained.

Further, as the distillation conditions in Method 2, conditions for usual purification by distillation of such fluorinated hydroxyl compound may be employed. Usually, the tower top temperature is preferably from 40 to 200° C., and the pressure is preferably from 0.05 to 0.5 MPa (gauge pressure). In this method, the fluorinated hydroxyl compound is obtainable as a distillate component, and therefore, there is a merit that the purity is high, and inclusion of distillation residues, etc. can be avoided.

In Method 2, it is preferred to add an acid removing agent after the distillation. As the acid removing agent, an organic base compound or an inorganic base compound may be mentioned. Specifically, a sodium methylate solution, a sodium ethylate solution, a sodium hydroxide solution and a potassium hydroxide solution, may be mentioned. The amount of the acid removing agent is preferably from 0.01 to 30 wt % (mass %), more preferably from 0.1 to 10 wt % (mass %), based on the fluorinated hydroxyl compound (Formula 1).

In Method 1 and Method 2, a solvent may or may not be introduced to the reaction system, but it is preferred that the solvent is not introduced, from the viewpoint of the efficiency for separation and the volume efficiency.

According to the purification method of the present invention, it is possible to readily separate an unshared electron pair compound which used to be hardly separated. The fluorinated hydroxyl compound (Formula 1) obtained after the distillation is, in a usual case, a fluorinated hydroxyl compound (Formula 1) of high purity wherein the amount of the unshared electron pair compound is at most 0.01 wt % (mass %), and such a compound can be used for various purposes without any problem.

EXAMPLES

Now, the present invention will be described in detail with reference Examples, but the present invention is by no means restricted by such Examples.

Reference Example 1

Into a 1 l hastelloy C autoclave, 408 g of methanol was charged, and tetrafluoroethylene was charged to the gas phase portion, whereupon the internal temperature was adjusted to 125° C. By a metering pump, a solution having 8.2 g of di-tert-butyl peroxide dissolved in 72 g of methanol, was supplied over a period of 16 hours. By an automatic valve, the pressure was set to be constant at the total pressure of 0.8 MPa (gauge pressure, the same applies hereinafter), and tetrafluoroethylene was continuously supplied to supplement the amount reduced by the reaction. The total amount of tetrafluoroethylene supplied, was 230 g. After cooling to 40° C., the reaction solution was analyzed by gas chromatography (GC), whereby a mixture comprising 2,2,3,3-tetrafluoropropanol and tert-butanol (weight ratio 98.5:1.5) was found to be formed.

Reference Example 2

The reaction was carried out in the same manner as in Reference Example 1 except that the amounts of methanol, tetrafluoroethylene and di-tert-butyl peroxide were changed, to obtain a mixture comprising 616.4 g of methanol, 233.4 g of 2,2,3,3-tetrafluoropropanol, 8.5 g of tert-butanol and 5.3 g of di-tert-butyl peroxide.

Example 1

Example for Purification By Means of a Solid Acid Catalyst

A mixture comprising 5.0 g of tert-butanol and 45.0 g of 2,2,3,3-tetrafluoropropanol, was added to 131 g of Nafion SAC, whereby refluxing under heating was carried out at 120° C. under atmospheric pressure. Upon expiration of 3 hours, distillation was carried out at 0.026 MPa and in a reflux ratio of 1/1 to obtain 42 g of a main fraction of 2,2,3,3-tetrafluoropropanol, at a tower top temperature of 70° C. The main fraction 2,2,3,3-tetrafluoropropanol was analyzed by GC, whereby the purity was found to be 99.7% (area % of the chromatogram, the same applies hereinafter).

Example 2

Example for Purification By an Addition of a Proton Source

To a mixture comprising 12.6 kg of tert-butanol and 828 kg of 2,2,3,3-tetrafluoropropanol, 4.3 wt % (mass %) of water was added, followed by distillation at 0.10 MPa and in a reflux ratio of 10/1 to distill 21.1 kg of an azeotropic distillate of water and tert-butanol at a still pot temperature of from 70 to 90° C. at a tower top temperature of from 65 to 82° C. Thereafter, as a acid removing agent, 5.6 wt % (mass %) of a 28% sodium methylate/methanol solution was added to obtain a fore-running fraction containing water, and then 612 kg of a main fraction of 2,2,3,3-tetrafluoropropanol was obtained at 0.026 MPa in a reflux ratio of 1/1 at a tower top temperature of 70° C. The 2,2,3,3-tetrafluoropropanol of the main fraction was analyzed by GC, whereby the purity was at least 99%, and tert-butanol was less than the detection limit.

Example 3

Example for Purification By a Solid Acid Catalyst

The mixture obtained in Reference Example 2 comprising 616.4 g of methanol, 233.4 kg of 2,2,3,3-tetrafluoropropanol, 8.5 g of tert-butanol and 5.3 g of di-tert-butyl peroxide, was added by itself to 60 g of Nafion SAC, followed by distillation. As a low boiling point initial fraction 1 up to the distillate temperature of 64° C. under room temperature in a reflux/distillate ratio of 3/1, a mixture comprising 220.1 g of methanol and 4.2 g of di-tert-butyl peroxide, was obtained. As a low boiling initial fraction 2 up to the distillate temperature of 100° C. under the same conditions, a mixture comprising 250.1 g of methanol and 2.5 g of tert-butanol, was obtained. Thereafter, distillation was carried out under reduced pressure at 0.026 MPa in a reflux/distillate ratio of 20/1, to obtain 198.5 g of a main fraction of 2,2,3,3-tetrafluoropropanol at a tower top temperature of 70° C. The 2,2,3,3-tetrafluoropropanol of the main fraction, was analyzed by GC, whereby the purity was 99.9%.

Comparative Example 1

After obtaining the fore-running fraction from a mixture comprising 18 g of tert-butanol and 1182 g of 2,2,3,3-tetrafluoropropanol, 865 g of a main fraction of 2,2,3,3-tetrafluoropropanol was obtained at 200 torr in a reflux ratio of 1/1 at a tower top-temperature of 70° C. The 2,2,3,3-tetrafluoropropanol of the main fraction was analyzed by GC, whereby the purity was 97%, and tertbutanol was 1.3%.

INDUSTRIAL APPLICABILITY

According to the method of the present invention, purification of a fluorinated hydroxyl compound (Formula 1) can be carried out in good yield by a simple operation under industrially practical conditions, whereby a fluorinated hydroxyl compound (Formula 1) of high purity containing substantially no unshared electron pair compound, which used to be difficult to separate, can be obtained.

The entire disclosure of Japanese Patent Application No. 11-233608 filed on Aug. 20, 1999 including specification, claims and summary are incorporated herein by reference in its entirety.

What is claimed is:

1. A method comprising
distilling a mixture comprising a fluorinated hydroxyl compound of formula 1 and an aliphatic tertiary alcohol by adding water as a proton source and heating the mixture to separate the aliphatic tertiary alcohol from the mixture, $$R^f\text{—}CR^1R^2\text{—}OH \quad \text{formula 1}$$

wherein
$R^f$ is a $C_{1-20}$ polyfluoroalkyl group, and
$R^1$ and $R^2$ are each independently, a hydrogen atom or a $C_{1-3}$ alkyl group.

2. The method of claim 1, wherein the fluorinated hydroxyl compound is at least one member selected from the group consisting of $CF_3CH_2OH$, $CF_3CF_2CH_2OH$, $CF_3(CF_2)_2CH_2OH$, $CF_3(CF_2)_3CH_2OH$, $HCF_2CH_2OH$, $H(CF_2)_2CH_2OH$, $H(CF_2)_3CH_2OH$, $H(CF_2)_4CH_2OH$, $CHF_2CF_2C(CH_3)_2OH$, $CF_3CHFCF_2CH_2OH$, $CF_3CHFCF_2CH(CH_3)OH$ and $CF_3CHFCF_2C(CH_3)_2OH$.

3. The method of claim 1, wherein the fluorinated hydroxyl compound has from 1 to 4 carbon atoms.

4. The method of claim 1, wherein the fluorinated hydroxyl compound has from 1 to 3 fluorine atoms bonded to the carbon atom that is directly bonded to the $CR^1R^2$—OH portion of the polyfluoroalkyl group.

5. The method of claim 1, wherein the mixture is a reaction crude product containing an alcohol compound of the following formula 3 and a compound of the following formula 1a formed by heating a perfluoroolefin compound of formula 2 and the alcohol compound of formula 3 in the presence of a radical initiator, $$R^{f1}CF\text{=}CF_2 \quad \text{formula 2}$$

$$CHR^1R^2OH \quad \text{formula 3}$$

$$R^{f1}CHFCF_2CR^1R^2OH \quad \text{formula 1a}$$

wherein,
$R^{f1}$ is a fluorine atom or a $C_{1-18}$ polyfluoroalkyl group, and
$R^1$ and $R^2$ are each independently, a hydrogen atom or a $C_{1-3}$ alkyl group.

6. The method of claim 5, wherein the mixture further comprises an unreacted radical initiator.

7. The method of claim 1, wherein the water is present in amount of from 0.01 to 30 mass % based on the fluorinated hydroxyl compound.

8. The method of claim 1, wherein the water is present in amount of from 0.1 to 10 mass % based on the fluorinated hydroxyl compound.

9. The method of claim 1, wherein the water is present in amount of from 1 to 10 mass % based on the fluorinated hydroxyl compound.

10. The method of claim 1, wherein the mixture is heated to a temperature of from 50 to 250° C.

11. The method of claim 1, wherein the mixture is heated to a temperature of from 50 to 130° C.

12. The method of claim 1, further comprising adding an acid removing agent to the mixture after distillation.

13. The method of claim 12, wherein the acid removing agent is an organic base compound or an inorganic base compound.

14. The method of claim 12, wherein the acid removing agent comprises an organic base compound selected from the group consisting of sodium methylate and sodium ethylate.

15. The method of claim 12, wherein the acid removing agent comprises an inorganic base compound selected from the group consisting of sodium hydroxide and potassium hydroxide.

16. The method of claim 1, further comprising collecting a main fraction of the distilled fluorinated hydroxyl compound having a purity of at least 99%.

17. The method of claim 1, wherein the tertiary alcohol is tert-butanol.

* * * * *